United States Patent [19]
Obermeier et al.

[11] Patent Number: 5,977,297
[45] Date of Patent: Nov. 2, 1999

[54] PROCESS FOR ISOLATING INSULIN BY HIGH-PRESSURE LIQUID CHROMATOGRAPHY

[75] Inventors: Rainer Obermeier, Hattersheim; Jürgen Ludwig, Brachttal; Walter Sabel, Bad Camberg, all of Germany

[73] Assignee: Hoechst Aktiengesellschaft, Frankfurt am Main, Germany

[21] Appl. No.: 08/992,676

[22] Filed: Dec. 17, 1997

[30] Foreign Application Priority Data

Dec. 18, 1996 [DE] Germany ............... 196 52 713

[51] Int. Cl.⁶ .................. A61K 38/28; A61K 38/00; C07K 5/00; C07K 7/00
[52] U.S. Cl. ............... 530/305; 530/303; 530/324; 530/344; 530/300
[58] Field of Search ............ 530/305, 324, 530/303, 344

[56] References Cited

U.S. PATENT DOCUMENTS

| | | | |
|---|---|---|---|
| 4,677,192 | 6/1987 | Obeimeier et al. | 530/305 |
| 5,621,073 | 4/1997 | Dickhardt et al. | 530/305 |

FOREIGN PATENT DOCUMENTS

| | | | |
|---|---|---|---|
| 0368187 | 5/1990 | European Pat. Off. | C07K 7/40 |

*Primary Examiner*—Avis M. Davenport
*Attorney, Agent, or Firm*—Finnegan, Henderson, Farabow, Garrett & Dunner, LLP

[57] ABSTRACT

A process for isolating insulin which entails performing high-pressure liquid chromatography with pressure-stable acidic cation exchange material under a pressure of from 1.1 MPa to 40 MPa.

38 Claims, No Drawings

PROCESS FOR ISOLATING INSULIN BY HIGH-PRESSURE LIQUID CHROMATOGRAPHY

BACKGROUND OF THE INVENTION

In the preparation of recombinant insulins, the microbial biosynthesis of the insulin takes place in bacteria such as transformed *Escherichia coli* via a single-chain precursor molecule which, besides the natural insulin sequence of the A and B chains, comprises a connecting peptide and a fusion protein sequence. The latter is connected to the N-terminal end of the complete protein for genetic engineering reasons, and is responsible for the expressed insulin-containing product resulting in the form of inclusion bodies in the transformed *E. coli*. The aim of the working up is to make the insulin available from this fusion protein in multistage protein-chemical process steps. This entails in every case, just like the natural biosynthesis of insulin in the beta cell of the pancreas, passing through the stage of folding to (pre) proinsulin. The (pre)proinsulin is converted by enzymatic cleavage (for example, with trypsin) into a cleavage mixture which comprises another insulin precursor, which is di-Arg-(B31-32)-insulin, mono-Arg-B31-insulin and the connecting peptide (up to 35 amino acid residues). Also produced are byproducts which are generated by the protease activity of the trypsin, such as incomplete intermediates, de-Thr-B30-insulin or else Arg-A0-insulin and preinsulin. U.S. Pat. No. 5,101,013 discloses the separation of said mixtures of insulin and insulin derivatives by atmospheric pressure or medium pressure chromatography on strongly acidic ion exchangers such as S-SEPHAROSE®, FRAKTOGEL®TSK or SP TRISACRYL®. The known chromatography materials are not pressure-stable and become compressed in the chromatography columns under a pressure of above 1 MPa. When the materials become compressed, [and] separation of the insulin-containing mixtures is then no longer possible.

Another known process for isolating insulin is high-pressure liquid chromatography on lipophilically modified silica gel (U.S. Pat. No. 5,245,008 and European Patent No. 0 547 544).

Cationic exchange purification processes using atmospheric pressure do not achieve, even with optimized traditional gel materials, the separation efficiencies necessary to attain the required degree of purification for the recombinant insulin. Chromatography with modern preparative gel materials, for example POROS 50 μm/Perseptiv, Source 30 μm/Pharmacia or MAKROPEP 50 μm/BioRad, is carried out in a medium pressure process. Medium pressure chromatography with gels of smaller particle size (for example, Source 15 μm) affords only slight selectivity improvements in respect of the separation efficiency, so that, in this case too, the last purification stage inevitably remains high-pressure liquid chromatography "HPLC" to eliminate extremely small impurities in the insulins. The disadvantages of reverse phase HPLC, such as risk of denaturation of the protein, bleeding of the RP silica gel phase, and unsatisfactory cleaning in place measures, must be accepted for this and require above-average expenditure of money and time.

SUMMARY OF THE INVENTION

In the endeavor to provide improved separation and isolation processes for obtaining insulin from enzymatic cleavage reactions, it has now been found that the same can be achieved by chromatography of the insulin and insulin derivative mixtures of pressure-stable acidic cation exchangers under a pressure of from from about 1.1 MPa to about 40 MPa. The insulin isolated in this way is suitable for direct use, without further purification steps, in injection solutions for treating diabetes mellitus. The invention therefore relates to a process for isolating insulin by chromatography, wherein the separation is carried out with pressure-stable acidic cation exchange materials under a pressure of from about 1.1 MPa to about 40 MPa.

The term insulin means compounds which are of animal or human origin, for example human insulin or porcine insulin, insulin precursors such as proinsulins or preinsulins, or recombinant insulins or insulin derivatives expressed by genetically modified microorganisms. Insulins can also be modified by chemical or enzymatic derivatization, for example, de-Phe-B1-insulin, diarginine-insulin (B31, B32), monoarginine-insulin, diphenylalanine-insulin (B31,B32) (U.S. Pat. No. 4,601,852), or $Gly^{A21}$-$Arg^{B31}$-$Arg^{B32}$-human insulin (European Patent No. 368 187).

The insulins preferably [employed] isolated in the process according to the invention have the formula I

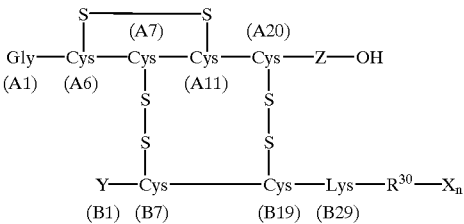

$R^{30}$ is the residue of a genetically encodable L-amino acid,

X is a hydroxyl group, a genetically encodable L-amino acid residue, n is an integer from 0 to 10, Y is hydrogen atom or L-phenylalanine residue, and Z is a genetically encodable L-amino acid residue; and where residues A2–A20 correspond to the amino acid sequence of the A chain of human insulin, animal insulin or an insulin derivative, and residues B2–B29 correspond to the amino acid sequence of the B chain of human insulin, animal insulin, or an insulin derivative.

Preferred insulins have the formula I where $R^{30}$ is a residue from the group of L-alanine and L-threonine, X is an L-amino acid residue from the group of L-arginine, L-lysine and L-phenylalanine, n is an integer from 0 to 6, and Z is a residue from the group of glycine, L-alanine, L-serine, L-threonine, L-aspartic acid and L-glutamic acid; and where A1 to A20 or B2 to B29 represent the amino acid sequence of human, porcine or bovine insulin.

DESCRIPTION OF THE PREFERRED EMBODIMENTS

It is particularly preferred to isolate human insulin and $Gly^{A21}$-$Arg^{B31}$-$Arg^{B32}$-human insulin.

The amino acid sequence A1 to A20 of human insulin is:

Gly Ile Val Glu Gln Cys Cys Thr Ser Ile Cys Ser
Leu Tyr Gln Leu Glu Asn Tyr Cys (SEQ ID NO: 1)

The amino acid sequence B1 to B29 of human insulin is:

Phe Val Asn Gln His Leu Cys Gly Ser His Leu

Val Glu Ala Leu Tyr Leu Val Cys Gly Glu Arg

Gly Phe Phe Tyr Thr Pro Lys (SEQ ID NO: 2)

Insulin can be employed both in the relatively contaminated state and in prepurified form (for example, by gel chromatography). Insulin is still contaminated, after repeated crystallization and even after gel chromatography, with insulin-like concomitant substances which are very similar in molecular weight and which, at a suitably chosen pH, differ in their charge state from one another and from insulin but form complexes with insulin (U.S. Pat. No. 4,129,560). Examples of such substances are:

Deamidoinsulin, arginine- and diarginine-insulin and insulin ethyl ester.

The term pressure-stable acidic cation exchange materials means, for example, materials such as a copolymer of polystyrene and divinylbenzene, which are modified with sulfo groups, in particular with R—O—CH$_2$—CHOH—CH$_2$—O—CH$_2$—CHOH—CH$_2$—SO$_3$-groups. The following products are particularly preferred:

Source 30S® supplied by Pharmacia Biotech AB, Uppsala, Sweden, pressure-stable, spherical and porous materials with a particle diameter of about 30 $\mu$m (Downstream, No 19, (1995), Pharmacia Biotech AB, S-751 82 Uppsala, Sweden, pages 3–8);

Source 15S® supplied by Pharmacia Biotech AB, Uppsala, Sweden, pressure-stable, spherical and porous materials with a particle diameter averaging 15 $\mu$m;

POROS® 50 $\mu$m, supplied by Perseptiv; and

MAKROPREP® 50 $\mu$m, supplied by Biorad.

The eluents contain a buffer substance which keeps the pH of the eluent constant, water, and organic solvents. Suitable buffer substances are disclosed in the literature, for example phosphates, alkali metal or alkaline earth metal salts, such as potassium acetate, ammonium citrate, sodium citrate, acetate, sulfate or chloride.

The eluents further contain water-miscible organic solvents such as alcohols, ketones, methyl acetate, dioxane or acetonitrile. (C$_1$–C$_4$) alcohols such as n- or iso-propanol, methanol, ethanol or butanol are preferably employed as the water-miscible organic solvents. The concentration of the water-miscible organic solvents for the chromatography is from about 10 to about 50% by volume, preferably from about 20 to about 40% by volume, particularly preferably being from about 25 to about 35% by volume. The concentration of the buffer substance is from about 1 mmol/l to about 140 mmol/l, based on water as solvent, preferably from about 2 mmol/l to about 120 mmol/l. Further additives which can be added to the buffer solution are, for example, salt, preferably physiologically tolerated mineral salt, one or more organic acids such as formic acid, acetic acid, lactic acid or citric acid, preferably lactic acid, a base, preferably NaOH, and/or preservatives. The preferred pH of the buffer solution is from about 2.5 to about 5.5, particularly preferably from about 3.5 to about 4.0. The concentration of the organic acid may vary within a wide range. Advantageous amounts are from about 10 to about 100 mmol/l, based on water as solvent, preferably from about 25 to about 50 mmol/l.

The temperature during the chromatography is from about 0° C. to about 50° C., preferably from about 15 to about 30° C., particularly preferably from about 15 to about 20° C. The operating pressure during the chromatography is substantially constant. The chromatography can be carried out using different pressures, for example the chromatography can be carried out under a pressure of from about 1.1 to about 40 MPa, in particular under 1.5 to 10 MPa. The eluent flow rates are from about 200 to about 1000 cm/h, maximum 2000 cm/h.

The loading of the columns, chromatography, and elution of the insulins and insulin derivatives take place by known, conventional technical methods. The loading of the column with the insulin solution to be purified preferably takes place using aqueous/alcoholic or purely aqueous buffer solution. The insulin solution has a protein content of from about 1 to about 10%, preferably about 3%.

The loading of the pressure-stable acidic cation exchanger can take place, for example, by dissolving the insulin mixture in a buffer solution—preferably having the composition described previously and having the pH described previously—and bringing the resulting solution into contact with the pressure-stable acidic cation exchanger.

The elution solution, which can in principle have a composition similar to that of the buffer solution described previously, preferably has a pH of from about 3.5 to about 4.0. A particularly suitable elution process is one in which the elution solution displays a time gradient of the salt concentration, preferably with a linear course. This concentration gradient can be applied, for example, by a low salt concentration being present in the elution solution at the start of the elution (which initially can be zero per cent salt), and by increasing the salt concentration during the elution process. It is possible in this way to achieve a particularly effective separation of the protein mixture. A preferred salt concentration gradient varies from near 0 mol of salt/l (at the start of the elution) to about 0.8 mol of salt/l (at the end of the elution), with the particular preferable range being from about 0.10 (at the start of the elution) to about 0.25 mol/l (at the end of the elution). Suitable added salts can be any of many organic and inorganic salts. Physiologically tolerated salts such as ammonium and alkali metal salts are preferred. Sodium salts are particularly preferred and sodium chloride is the preferred sodium salt.

The separation process according to the invention takes place in a column process. The temperature, which is preferably kept constant during the ion exchange chromatography, may be varied within a wide range. A preferred temperature range is from about –10° C. to about 50° C., in particular from about 15 to about 25° C.

Concentrating the insulin after the chromatography from the eluates takes place by precipitation with zinc salt or by crystallization. It is possible optionally for the solvent to have previously been substantially removed from the solution by distillation under reduced pressure, or for its concentration to have been reduced by dilution with water. In either approach, the solvent concentration should be 10% or less before the precipitation or crystallization, in order to keep the protein content in the supernatant at less than about 50 mg/liter. The resulting insulin precipitates can be isolated by decantation, centrifugation, or filtration, and then can be dried. The process according to the invention is suitable not only for analytical chromatography but also for preparative chromatography, in particular when the process according to the invention is carried out with a preparative high-pressure liquid chromatography "HPLC" system.

The term "preparative chromatography" is used herein to mean[s] a purification process with the aim of isolating, and not merely analyzing, pure products in each chromatography run. The amount of pure products may vary within wide limits, for example from about 1 mg to about 5.0 kg, preferably from about 50 mg to about 2.5 kg.

The process according to the invention is described in detail in the following examples. Percentage data are based on volume unless indicated otherwise.

EXAMPLE 1

Buffer A: 30% n-propanol, 50 mM lactic acid, 0.01 M NaCl in water, pH 3.5

Sorbent: Source S 15® µm

Column dimensions: 5 cm×25 cm.

A preparative HPLC column (5 cm×25 cm, column volume approximately 500 ml) is packed with a suspension of Source S15 µm in 50% aqueous ethanol and equilibrated with Buffer A. For this purpose, the buffer is pumped onto the column at a flowrate of 98 ml/minute. A pressure of 1.9 MPa builds up during this. The column is in this case part of a chromatography system with a fractionation collector and UV detector (254/280 nm).

Five grams of the crude recombinant human insulin to be purified are dissolved in 500 ml of Buffer A and pumped onto the column at the same flowrate as above. Renewed equilibration is carried out with 1000 ml of Buffer A during a subsequent washing period. For elution, a linear NaCl gradient composed of Buffer A and Buffer B (Buffer B=Buffer A+0.15 M NaCl) is pumped via a gradient mixing system onto the low pressure side of the column, and a UV elution diagram is obtained. The eluate is fractionated, and the individual fractions are checked by a conventional analytical HPLC method. Fractions which correspond to the required purity are combined. After dilution with water (1 vol. of eluate+2 vol. of water), the highly purified insulin is isolated by crystallization as $Zn^{2+}$ insulin by known processes. The yield of the process was 3.8 g with a purity of greater than 98% as determined by the HPLC analysis which is described below.

HPLC Analysis 12.5 mg of protein containing insulin are dissolved in 25 ml of eluent C (see eluents) and 0.02 ml of this solution is loaded onto a high-pressure liquid chromatography column which comprises ET 25018/4 NUCLEOSIL®300-5 $C_{18}$ (Macherey & Nagel, Aachen, Germany).

Eluents:

Stock solution:

41.4 g of sodium dihydrogen phosphate * $H_2O$ 1800 ml of double-distilled water adjusted to pH 2.5 with 85% phosphoric acid and make up to 000 ml with double-distilled water Eluent C:

500 ml of stock solution 500 ml of acetonitrile 1000 ml of double-distilled water Eluent D:

500 ml of stock solution 1300 ml of acetonitrile 200 ml of double-distilled water 6.4 g of sodium chloride Gradient:

| TIME | % C | % D |
|---|---|---|
| 0 min | 96 | 4 |
| 6 min | 91 | 9 |
| 15 min | 91 | 9 |
| 25 min | 85 | 15 |
| 30 min | 65 | 35 |
| 32 min | 10 | 90 |
| 35 min | 96 | 4 |
| 45 min | 96 | 4 |

The slope of the gradient should be adjusted so that the main peak of the insulin is eluted after 17 to 21 min.

Temperature: 40° C.

Total running time: 45 min,

Flow rate: 1 ml/min

Detection: 210 nm

EXAMPLE 2

Five grams of a mixture of de-$Thr^{B30}$-human insulin (insulin from Seq ID No. 1 and No. 3 with correct cystine bridges), Arg-B31-human insulin (insulin from Seq ID No. 1 and No. 5 with correct cystine bridges), and $Gly^{A21}$-$Arg^{B31}$-$Arg^{B32}$-human insulin (insulin from Seq ID No. 6 and No. 4 with correct cystine bridges) are purified as in Example 1. The mixture is typically produced in the isolation of recombinant insulin. Said mixture furthermore contains, because of non-specific enzymatic cleavages, very small amounts of other impurities whose concentration must be reduced to give the medicinal substance ready for use.

The various components are eluted as in Example 1. The UV diagram shows a selective separation of the individual components according to increasing isoelectric point with increasing NaCl gradient (de-$Thr^{B30}$-human insulin:I; $Arg^{B31}$-human insulin: II; $Gly^{A21}$-$Arg^{B31}$-$Arg^{B32}$-human insulin: III). The fractionated column eluate is analyzed as in Example 1, and the required high-purity product $Gly^{A21}$-$Arg^{B31}$-$Arg^{B32}$-human insulin is isolated by crystallization. The yield of the process was 1.78 g with a purity of greater than 98.5% (determined by HPLC analysis).

EXAMPLE 3

Comparative example of the present invention and the prior art. Five grams of a mixture as in Example 2 are purified under the conditions of medium pressure chromatography under 1 MPa (10 bar) with an eluent flow rate of 39 ml/min. The UV elution diagram shows a similar separation of the components as in Example 2. However, it is evident merely from the course of this diagram that the sharpness of separation of the individual compounds is less. The HPLC analysis confirms a distinct overlap of the individual insulin impurities. The purified product is isolated by crystallization. Despite a lower yield, the purity does not comply with the required specification of the medicinal substance. Preparation thereof requires a subsequent preparative HPLC purification on reverse phase silica gel. The yield of the process was 1.5 g of $Gly^{A21}$-$Arg^{B31}$-$Arg^{B32}$-human insulin with a purity of greater than 97.6% (determined by HPLC analysis).

What is claimed is:

1. A process for isolating an insulin by chromatography comprising the steps of:

(a) obtaining a column comprising pressure-stable acidic cation exchange material;

(b) loading the column with a sample solution including an insulin;

(c) performing chromatography; and (d) eluting the insulin from the column with an eluting solution;

said process being performed under a pressure of from about 1.1 MPa to about 40 MPa.

2. The process for isolating an insulin by chromatography as claimed in claim 1, wherein the isolated insulin has a formula I of:

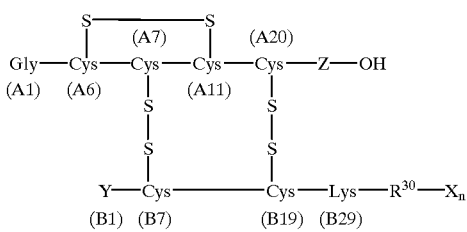

wherein $R^{30}$ is the residue of a genetically encodable L-amino acid,

X is a hydroxyl group, or a genetically encodable L-amino acid residue, n is an integer from 0 to 10, Y is hydrogen atom or L-phenylalanine residue, and Z is a genetically encodable L-amino acid residue;

wherein residues A2–A20 correspond to the amino acid sequence of the A chain of human insulin, animal insulin, or an insulin derivative; and wherein residues B2–B29 correspond to the amino acid sequence of the B chain of human insulin, animal insulin or an insulin derivative.

3. The process for isolating an insulin by chromatography as claimed in claim 2, wherein the isolated insulin derivative has a formula I:

wherein $R^{30}$ is L-alanine or L-threonine,

X is an L-amino acid from the group of L-arginine, L-lysine or L-phenylalanine, Z is glycine, L-alanine, L-serine, L-threonine, L-aspartic acid or L-glutamic acid, and n is an integer from zero to 6; and wherein A1 to A20 or B2 to B29 represents the amino acid sequence of human, porcine, or bovine insulin.

4. The process for isolating an insulin by chromatography as claimed in claim 1, wherein the isolated insulin is human.

5. The process for isolating an insulin by chromatography as claimed in claim 2, wherein the isolated insulin is human.

6. The process for isolating an insulin by chromatography as claimed in claim 3, wherein the isolated insulin is human.

7. The process for isolating an insulin by chromatography as claimed in claim 1, wherein the eluting step is performed using an $H_2O/(C_1-C_4)$ alkanol mixture which comprises from about 10 to about 50 percent by volume of $(C_1-C_4)$ alkanol.

8. The process for isolating an insulin by chromatography as claimed in claim 1, wherein the eluting step is performed using an $H_2O/(C_1-C_4)$ alkanol mixture which comprises from about 20 to about 40 percent by volume of $(C_1-C_4)$ alkanol.

9. The process for isolating an insulin by chromatography as claimed in claim 1, wherein the eluting step is performed using an $H_2O/(C_1-C_4)$ alkanol mixture which comprises from about 25 to about 35 percent by volume of $(C_1-C_4)$ alkanol.

10. The process for isolating an insulin by chromatography as claimed in claim 1, wherein the pressure-stable acidic cation exchanger is a crosslinked polymer of polystyrene and divinylbenzene with sulfo groups.

11. The process for isolating an insulin by chromatography as claimed in claim 2, wherein the pressure-stable acidic cation exchanger is a crosslinked polymer of polystyrene and divinylbenzene with sulfo groups.

12. The process for isolating an insulin by chromatography as claimed in claim 3, wherein the pressure-stable acidic cation exchanger is a crosslinked polymer of polystyrene and divinylbenzene with sulfo groups.

13. The process for isolating an insulin by chromatography as claimed in claim 1, wherein the loading step is performed with a sample solution comprising from about 5 to about 15 g of protein per liter column volume at a pH of from 2.5 to 5.5.

14. The process for isolating an insulin by chromatography as claimed in claim 5, wherein the loading step is performed with a sample solution comprising from about 5 to about 15 g of protein per liter column volume at a pH of from 2.5 to 5.5.

15. The process for isolating an insulin by chromatography as claimed in claim 8, wherein the loading step is performed with a sample solution comprising from about 5 to about 15 g of protein per liter column volume at a pH of from 2.5 to 5.5.

16. The process for isolating an insulin by chromatography as claimed in claim 1, wherein the loading step is performed with a sample solution comprising from about 5 to about 15 g of protein per liter column volume at a pH of from 3.5 to 4.0.

17. The process for isolating an insulin by chromatography as claimed in claim 5, wherein the $H_2O/(C_1-C_4)$ alkanol mixture used for the eluting solution comprises ethanol, isopropanol, or propanol, as the $(C_1-C_4)$ alkanol.

18. The process for isolating an insulin by chromatography as claimed in claim 1, wherein the pH of the eluting solution is adjusted to 3.5 to 4.0.

19. The process for isolating an insulin by chromatography as claimed in claim 5, wherein the pH of the eluting solution is adjusted to 3.5 to 4.0.

20. The process for isolating an insulin by chromatography as claimed in claim 8, wherein the pH of the eluting solution is adjusted to 3.5 to 4.0.

21. The process for isolating an insulin by chromatography as claimed in claim 1, wherein the loading solution comprises a buffer substance.

22. The process for isolating an insulin by chromatography as claimed in claim 8, wherein the loading solution comprises a buffer substance.

23. The process as claimed in claim 21, wherein the buffer substance is based on an organic acid.

24. The process as claimed in claim 21, wherein the buffer substance is lactic acid.

25. The process for isolating an insulin by chromatography as claimed in claim 1, wherein the eluting solution comprises a buffer substance.

26. The process for isolating an insulin by chromatography as claimed in claim 25, wherein the buffer substance is based on an organic acid.

27. The process for isolating an insulin by chromatography as claimed in claim 25, wherein the buffer substance is lactic acid.

28. The process for isolating an insulin by chromatography as claimed in claim 1, wherein the loading and eluting solution each comprise a buffer substance.

29. The process for isolating an insulin by chromatography as claimed in claim 28, wherein the buffer substance is based on an organic acid.

30. The process for isolating an insulin by chromatography as claimed in claim 28, wherein the buffer substance is lactic acid.

31. The process for isolating an insulin by chromatography as claimed in claim 1, wherein the eluting step is performed with an ammonium or alkali metal salt gradient from 0 to 0.8 mol/liter.

32. The process for isolating an insulin by chromatography as claimed in claim 1, wherein the eluting step is performed with an ammonium or alkali metal salt gradient from 0.10 to 0.25 mol/liter.

33. The process for isolating an insulin by chromatography as claimed in claim 1, wherein the process is performed under a pressure of from about 1.5 to about 10 MPa.

34. The process for isolating an insulin by chromatography as claimed in claim 5, wherein the process is performed under a pressure of from about 1.5 to about 10 MPa.

35. The process for isolating an insulin by chromatography as claimed in claim 8, wherein the process is performed under a pressure of from about 1.5 to about 10 MPa.

36. The process for isolating an insulin by chromatography as claimed in claim 10, wherein the process is performed under a pressure of from about 1.5 to about 10 MPa.

37. The process for isolating an insulin by chromatography as claimed in claim 13, wherein the process is performed under a pressure of from about 1.5 to about 10 MPa.

38. The process for isolating an insulin by chromatography as claimed in claim 16, wherein the process is performed under a pressure of from about 1.5 to about 10 MPa.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Escherichia coli (xi) SEQUENCE DESCRIPTION: SEQ ID NO:1:

Gly Ile Val Glu Gln Cys Cys Thr Ser Ile Cys Ser Leu Tyr Gln Leu
1               5                   10                  15

Glu Asn Tyr Cys Asn
            20

(2) INFORMATION FOR SEQ ID NO:2:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Escherichia coli (xi) SEQUENCE DESCRIPTION: SEQ ID NO:2:

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

(2) INFORMATION FOR SEQ ID NO:3:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Escherichia coli (xi) SEQUENCE DESCRIPTION: SEQ ID NO:3:

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25

(2) INFORMATION FOR SEQ ID NO:4:

(i) SEQUENCE CHARACTERISTICS:
        (A) LENGTH: 32 amino acids
        (B) TYPE: amino acid
        (C) STRANDEDNESS: single

```
            (D) TOPOLOGY: linear (ii) MOLECULE TYPE: peptide (vi) ORIGINAL SOURCE:
            (A) ORGANISM: Escherichia coli (xi) SEQUENCE DESCRIPTION: SEQ ID NO:4:

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

(2) INFORMATION FOR SEQ ID NO:5:

(i) SEQUENCE CHARACTERISTICS:
            (A) LENGTH: 31 amino acids
            (B) TYPE: amino acid
            (C) STRANDEDNESS: single
            (D) TOPOLOGY: linear (ii) MOLECULE TYPE: peptide (vi) ORIGINAL SOURCE:
            (A) ORGANISM: Escherichia coli (xi) SEQUENCE DESCRIPTION: SEQ ID NO:5:

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg
            20                  25                  30

(2) INFORMATION FOR SEQ ID NO:6:

(i) SEQUENCE CHARACTERISTICS:
            (A) LENGTH: 21 amino acids
            (B) TYPE: amino acid
            (C) STRANDEDNESS: single
            (D) TOPOLOGY: linear (ii) MOLECULE TYPE: peptide (vi) ORIGINAL SOURCE:
            (A) ORGANISM: Escherichia coli (xi) SEQUENCE DESCRIPTION: SEQ ID NO:6:

Gly Ile Val Glu Gln Cys Cys Thr Ser Ile Cys Ser Leu Tyr Gln Leu
1               5                   10                  15

Glu Asn Tyr Cys Gly
            20
```